United States Patent
Sung et al.

(10) Patent No.: US 9,623,121 B2
(45) Date of Patent: Apr. 18, 2017

(54) OPTICAL-IMAGING PROBE FOR DETECTING SENTINEL LYMPH NODES WHICH CONTAINS A COMPOSITE OF POLY-GAMMA-GLUTAMIC ACID AND AN OPTICAL-IMAGING DYE

(75) Inventors: Moon-Hee Sung, Daejeon (KR); Yong Taik Lim, Daejeon (KR); Young-Woock Noh, Daejeon (KR); Il Han Lee, Daejeon (KR)

(73) Assignees: BIOLEADERS CORPORATION, Daejeon (KR); THE INDUSTRY AND ACADEMIC COOPERATION IN CHUNGNAM NATIONAL UNIVERSITY, Daejeon (KR); KOOKMIN UNIVERSITY INDUSTRY - ACADEMIC COOPERATION FOUNDATION, Seoul (KR)

( * ) Notice: Subject to any disclaimer, the term of this patent is extended or adjusted under 35 U.S.C. 154(b) by 705 days.

(21) Appl. No.: 13/885,126

(22) PCT Filed: Nov. 18, 2011

(86) PCT No.: PCT/KR2011/008828
§ 371 (c)(1),
(2), (4) Date: Jul. 2, 2013

(87) PCT Pub. No.: WO2012/067458
PCT Pub. Date: May 24, 2012

(65) Prior Publication Data
US 2014/0161727 A1     Jun. 12, 2014

(30) Foreign Application Priority Data

Nov. 18, 2010   (KR) .................. 10-2010-0114925

(51) Int. Cl.
  *A61B 5/055*   (2006.01)
  *A61K 49/00*   (2006.01)
  *G01N 21/64*   (2006.01)
(52) U.S. Cl.
  CPC ...... *A61K 49/0054* (2013.01); *A61K 49/0034* (2013.01); *A61K 49/0056* (2013.01); *G01N 21/6428* (2013.01); *G01N 21/6456* (2013.01)
(58) Field of Classification Search
  CPC ........... A61B 6/48; A61B 6/481; A61B 6/487; A61K 49/00; A61K 49/0017; A61K 49/0041; A61K 49/003; A61K 49/0028; A61K 49/0034
  USPC ................... 424/9.1, 9.2, 9.341, 9.6
  See application file for complete search history.

(56) References Cited

U.S. PATENT DOCUMENTS

| | | | |
|---|---|---|---|
| 4,338,158 A | 7/1982 | Bentvelzen | |
| 5,532,350 A | 7/1996 | Cottrell et al. | |
| 5,898,033 A * | 4/1999 | Swadesh | A61K 47/48315 514/224.2 |
| 6,048,515 A | 4/2000 | Kresse et al. | |
| 6,159,445 A * | 12/2000 | Klaveness | B82Y 5/00 424/9.1 |
| 2004/0247655 A1 | 12/2004 | Asmus et al. | |
| 2007/0202075 A1 | 8/2007 | Hadba et al. | |
| 2008/0152615 A1 | 6/2008 | Sung et al. | |
| 2009/0180966 A1 | 7/2009 | Borbely et al. | |
| 2009/0285760 A1 | 11/2009 | Ishikawa et al. | |
| 2010/0047356 A1 | 2/2010 | Yu et al. | |

FOREIGN PATENT DOCUMENTS

| | | |
|---|---|---|
| EP | 1723855 B1 | 11/2006 |
| KR | 10-2009-0008838 A | 1/2009 |
| KR | 10-2009-0026642 A | 3/2009 |
| WO | 2009139466 A1 | 11/2009 |
| WO | 2010063701 A2 | 6/2010 |

OTHER PUBLICATIONS

Melancon et al (Development of a macromolecular Dual-Modality MR-Optical Imaging for Sentinel Lymph Node Mapping; Investigative Radiology, vol. 42, No. 8 Aug. 2007, pp. 569-578).*
Melancon et al (Development of macromolecular Dual-Modality MR Optical Imaging for Sentinel Lymph Node Mapping; Investigative Radiology, vol. 42, No. 8, Aug. 2007, pp. 569-579).*
McCorquodale et al (Indocyanine Green as a noncovalent, pseudofluorogenic label for protein determination by capillary electrophoresis, Electrophoresis, vol. 22, pp. 2403-2408, 2001).*
He, X., et al., "In vivo near-infrared fluorescence imaging of cancer with nanoparticle-based probes", "WIREs Nanomed Nanobiotechnol", Jul./Aug. 2010, pp. 349-366, vol. 2.
Melancon, M., et al., "Development of a Macromolecular Dual-Modality MR-Optical Imaging for Sentinel Lymph Node Mapping", "Invest Radiol.", Aug. 2007, pp. 569-578, vol. 42, No. 8.
Murawa, D., et al., "Sentinel lymph node biopsy in breast cancer guided by indocyanine green fluorescence", "British Journal of Surgery", Nov. 2009, pp. 1289-1294, vol. 96.
Nakagawa, S., "Efficacy and Safety of Poly (gamma-glutamic acid) Based Nanoparticles (gamma-PGA NPs) as Vaccine Carrier", "Yakugaku Zasshi", Nov. 2008, pp. 1559-1565 (English Abstract, Figures, and Tables), vol. 128, No. 11.

* cited by examiner

*Primary Examiner* — Micah-Paul Young
(74) *Attorney, Agent, or Firm* — Hultquist, PLLC; Steven J. Hultquist

(57) ABSTRACT

The present invention relates to an optical imaging probe for detecting a sentinel lymph node, which contains a complex of poly-gamma-glutamic acid and an optical imaging dye, and more particularly to an optical imaging probe for detecting a sentinel lymph node, which contains a poly-gamma-glutamic acid/optical imaging dye complex that, when injected subcutaneously in vivo, remains in the sentinel lymph node for a relatively long period of time and has a low tendency to migrate to other lymph nodes. The present invention provides a poly-gamma-glutamic acid/fluorescent dye complex, which contains no radiopharmaceutical and is harmless to the human body. The use of the poly-gamma-glutamic acid/fluorescent dye complex makes it possible to accurately detect the position of a sentinel lymph node in real time without concerns about radioactive contamination.

1 Claim, 2 Drawing Sheets

OPTICAL-IMAGING PROBE FOR DETECTING SENTINEL LYMPH NODES WHICH CONTAINS A COMPOSITE OF POLY-GAMMA-GLUTAMIC ACID AND AN OPTICAL-IMAGING DYE

CROSS-REFERENCE TO RELATED APPLICATIONS

This application is a U.S. national phase under the provisions of 35 U.S.C. §371 of International Patent Application No. PCT/KR2011/08828 filed Nov. 18, 2011, which in turn claims priority of Republic of Korea Patent Application No. 10-2010-0114925 filed Nov. 18, 2010. The disclosures of such international patent application and Republic of Korea priority patent application are hereby incorporated herein by reference in their respective entireties, for all purposes.

TECHNICAL FIELD

The present invention relates to an optical imaging probe for detecting a sentinel lymph node, which contains a complex of poly-gamma-glutamic acid and an optical imaging dye, and more particularly to an optical imaging probe for detecting a sentinel lymph node, which contains a poly-gamma-glutamic acid/optical imaging dye complex that, when injected subcutaneously in vivo, remains in the sentinel lymph node for a relatively long period of time and has a low tendency to migrate to other lymph nodes.

BACKGROUND ART

Anatomically, the sentinel lymph node can be defined as the first node that receives lymphatic drainage from a primary tumor. If whether tumor cells in the sentinel lymph node are benign or malignant is determined, whether other lymph nodes contain metastatic tumor can be determined. Thus, if whether the sentinel lymph node contains metastatic tumor cells is determined, the status of other lymph nodes can also be predicted.

In other words, if the sentinel lymph node contains no tumor cells, it can appear that other lymph nodes also contain no tumor cells. Methods for detecting the sentinel lymph node include a method that uses isosulfan blue dye (isosulfan blue dye, Lymphazurin 1%, Ben Venue Lab., Inc., USA) as a visual aid during a surgical operation, and a method utilizing a hand-held gamma probe, which comprises injecting technetium-99m colloid albumin into a patient before a surgical operation, and then identifying radioactive lymph nodes with a Neoprobe 1500 (Neoprobe Corp, USA). When the two methods are used in combination, the sentinel lymph node can be almost completely identified. Thus, a surgical technique of identifying the sentinel lymph node and predicting the metastasis of tumor cells to other lymph nodes based on the identified sentinel lymph node has been increasingly used.

In the case of superficial cancers, like melanoma or breast cancer, when the sentinel lymph node is identified and applied surgically, unnecessary lymph node excision can be avoided. Wide local excision or radical vulvectomy, including unilateral or bilateral lymphadenectomy, is a palliative surgical method that is performed in vulvar cancer patients, and is often accompanied by sequelae such as wound breakdown, lymphoedema or lymphoma. Thus, this surgical technique is not preferable in terms of the patient's life quality, even though it is successful.

However, if the sentinel lymph node is identified and a frozen biopsy thereof is determined to be benign after whether other lymph nodes contain metastatic tumor cells is determined based on the frozen biopsy, a surgical operation can be achieved by exercising only the sentinel lymph node. This method can appear to be a highly advanced method for surgery of vulvar cancer.

However, conventional methods for detecting the sentinel lymph node using radiopharmaceuticals have many problems. Specifically, the contamination of an analyzer and an analysis room during the pathological analysis of a lymph node labeled with a radiopharmaceutical, and the disposal of a sample after pathological analysis become serious problems. Particularly, there is an urgent need for development of a method of detecting the sentinel lymph node using molecular imaging methods other than nuclear medicine methods so as to minimize the radiation exposure of patients.

In an attempt to overcome these problems, the present inventors have made efforts to develop a novel method capable of effectively detecting the sentinel lymph node using a complex of a biocompatible polymer and a biocompatible optical imaging probe.

Indocyanine Green (ICG) is a typical biocompatible optical imaging probe showing fluorescent characteristics in a near-infrared region (700-1300 nm) and is a unique near-infrared fluorescent probe approved for human use by the FDA. Near-infrared rays have advantages over visible rays in that they have high skin permeability, and thus make it possible to obtain molecular images of subcutaneous blood vessels or organs or can provide guidance to sensitive portions such as nerves or blood vessels during a surgical operation.

Indocyanine green (ICG) is used mainly in liver function tests in which ICG is injected intravenously and whether ICG remains in blood is examined at a specific time after injection. ICG binds to serum protein, is absorbed selectively by the liver, and is excreted into bile without being excreted into the kidneys. Thus, in this test method, liver functions can be examined by measuring the retention rate or removal rate of the ICG dye in blood. A retention rate of 5% or less at 15 min is a normal value, and a retention rate of 10% or more means a severe impairment in liver function caused by cirrhosis or the like.

Although ICG was used in studies on the detection of the sentinel lymph node, but there were problems in that ICG has a too small size, and thus when it is injected in vivo, it does not remain in the sentinel lymph node for a long period of time and migrates to other surrounding lymph nodes. This makes it difficult to distinguish the sentinel lymph node from lymph nodes around cancer tissue during an actual surgical operation.

Recently, a patent application was made, which is related to polymer particles containing a near-infrared fluorescent dye, which are prepared by dispersing an aqueous solution of the near-infrared fluorescent dye indocyanine green (ICG) in an organic polymer solution and dispersing the resulting dispersion in an aqueous emulsifier solution (Korean Patent Laid-Open Publication No. 2009-0026642). Such polymer particles are nano/micro-sized particles having a particle diameter of more than 100 nm can be used mainly for intravenous administration and oral administration, but are not suitable for the detection of the sentinel lymph node, which requires a particle diameter of 10-25 nm.

In addition, a patent application was made, which is related to cell-encapsulated microcapsules containing indocyanine green, which are prepared by the ionic reaction of the biocompatible anionic polymer sodium alginate with the multiple cationic polymer poly-L-lysine solution (Korean Patent Laid-Open Publication No. 2009-0008838). However, such polymer particles are not suitable for the detection of the sentinel lymph node, because they have a particle diameter of more than 10 μm for cell encapsulation.

In addition, US Patent Publication No. 20100047356 discloses microcapsules prepared by encapsulating indocyanine green by the ionic reaction of a positively charged polyelectrulyte such as poly allylamine hydrochloride and a negative charged ion such as disodium, followed by coating with silica nanoparticles. Such polymer microcapsules have a particle diameter of 0.6-2 μm and are used in photodynamic therapy based on the characteristics of indocyanine green, but are not suitable for the detection of the sentinel lymph node.

Accordingly, the present inventors have made extensive efforts to develop a molecular imaging probe which, when injected into blood, remains in the sentinel lymph node for an extended period of time and has a low tendency to migrate to other lymph nodes. As a result, the present inventors have prepared a complex of poly-gamma-glutamic acid (γ-PGA) and indocyanine green and have found that, when the complex is used as a molecular imaging probe, the sentinel lymph node can be detected in a more easy and accurate manner, thereby completing the present invention.

SUMMARY OF INVENTION

It is an object of the present invention to provide an optical imaging probe for detecting a sentinel lymph node, which contains a complex of poly-gamma-glutamic acid and an optical imaging dye, in which the optical imaging probe serving as a molecular imaging probe remains in the sentinel lymph node for an extended period of time and has a reduced tendency to migrate to other lymph nodes so that the sentinel lymph node can be detected in an easier and more effective manner.

To achieve the above object, the present invention provides an optical imaging probe for detecting a sentinel lymph node, which contains a complex of poly-gamma-glutamic acid and an optical imaging dye.

Other features and embodiments of the present invention will be more apparent from the following detailed descriptions and the appended claims.

BRIEF DESCRIPTION OF THE DRAWINGS

FIG. 1 shows the fluorescence intensity measured after dispensing 50 μl of each of 0.01% ICG and a γ-PGA/ICG complex solution into a 1.5 Ml tube, and then allowing the tubes to stand at room temperature for 3 days, in order to examine the light stability of each of ICG and the γ-PGA/ICG complex.

BEST MODE FOR CARRYING OUT THE INVENTION

Figure 1:
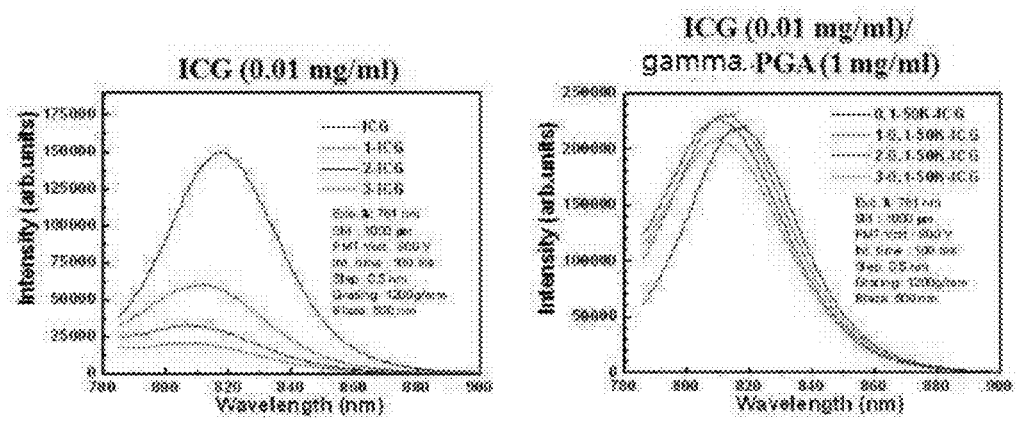
FIG. 1 shows the near-infrared fluorescence spectra of indocyanine green (ICG) (left) and a γ-PGA/ICG complex (right). Specifically.

In one aspect, the present invention is directed to an optical imaging probe for detecting a sentinel lymph node, which contains a complex of poly-gamma-glutamic acid and an optical imaging dye.

Indocyanine green which is used as a fluorescent dye is an anionic amphipathic (hydrophobic and hydrophilic) material. The negative charge of indocyanine is hydrophobically (non-covalently) coupled to the hydrophobic moiety of poly-gamma-glutamic acid (γ-PGA) in an aqueous solution to form a complex.

The optical imaging dye that is used in the present invention is a fluorescent dye that shows fluorescent characteristics in the visible and near-infrared wavelength regions. Particularly, an imaging probe comprising a near-infrared optical dye showing fluorescent characteristics in the near infrared wavelength region in which the skin penetration of light is the highest can sense a signal having a high S/N ratio.

In the present invention, the optical imaging dye may be a fluorescent dye of a near-infrared or visible ray region. The near-infrared fluorescent dye may be selected from the group consisting of Alexa Fluor 647, Alexa Fluor 660, Alexa Fluor 680, Alexa Fluor 700, Alexa Fluor 780, cy5, cy5.5, cy7, indocyanine green (ICG), Cypate, ITCC, NIR820, NIR2, IRDye680, IRDye700, IRDye800, DiD, DiR, Cresy Violet, Nile Blue, Oxazine 750, and Rhodamine 800, and the visible fluorescent dye may be selected from the group consisting of Alexa Fluor 350, Alexa Fluor 488, Alexa Fluor 532, Alexa Fluor 568, Alexa Fluor 633, Alexa Fluor 647, cy2, cy3, cy3.5, Fluorescein (FITC), NBD, Nile Red, Rhodamine B, Tetramethylrhodamine (TRITC), and Texas Red.

Preferably, the optical imaging dye may be a near-infrared fluorescent dye, and more preferably indocyanine green (ICG).

In the present invention, the optical imaging probe may be used to detect a sentinel lymph node.

γ-PGA that is used in the present invention is produced by microorganisms, and glutamic acid that is the constituent amino acid of γ-PGA has two isomers, D-glutamic acid and L-glutamic acid. Microorganisms reported to produce γ-PGA include *Natrialba aegyptiaca* and *Bacillus halodurans*, which produce a poly-gamma-glutamic acid consisting only of 100% L-glutamic acid, *Bacillus anthracis* produces a poly-gamma-glutamic acid consisting only of 100% D-glutamic acid, and *Bacillus licheniformis, Bacillus magaterium*, and *Bacillus subtilis*, which produce a poly-gamma-glutamic acid consisting of a mixture of D-glutamic acid and L-glutamic acid. The poly-gamma-glutamic acid that is used in the present invention may be any one of poly-gamma-D-glutamic acid, poly-gamma-L-glutamic acid and poly-gamma-D/L-glutamic acid. The poly-gamma-glutamic acid that is used in the present invention preferably has a molecular weight of 10-15000 kDa.

The near-infrared fluorescent dye that is used in the present invention may be selected from among cyanine fluorescent dyes, including cy3.5, cy5, cy5.5, cy7, and ICG. In addition, the near-infrared fluorescent dye that is used in the present invention may be an organic material selected from the group consisting of Alexa Fluor 647, Alexa Fluor 660, Alexa Fluor 680, Alexa Fluor 700, Alexa Fluor 780, Cypate, ITCC, NIR 820, NIR 2, IR Dye 680, IR Dye 700, IR Dye 800, DiD, DiR, Cresy Violet, Nile Blue, Oxaines, including Cresy Violet, Nile Blue, Oxazine 750, and Rhodamines, including Rhodamine 800 and Texas Red, but is not limited thereto.

As described above, indocyanine green (ICG) is one of several fluorescent dyes approved for human use by the FDA and emits fluorescence in a near-infrared wavelength region. Thus, it is used in various applications. However, it has low light stability which limits the use thereof.

To use ICG for detection of the sentinel lymph node, the present invention provides a method of significantly improving the light stability of ICG by forming a γ-PGA/ICG complex (see FIG. 1). As shown in FIG. 1, the fluorescence intensity of ICG rapidly decreased after 3 days, but the fluorescence intensity of the γ-PGA/ICG complex is maintained at a substantially constant level.

In addition, when ICG is administered in vivo in order to detect the sentinel lymph node, ICG does not remain in the sentinel lymph node for a long period of time and migrates to other surrounding lymph nodes, because ICG has a low molecular weight. Thus, the present invention provides a solution to this problem. This problem makes it difficult to distinguish the sentinel lymph node from lymph nodes around cancer tissue during an actual surgical operation. To overcome this problem, the present invention provides a complex of ICG with a biocompatible polymer having a high molecular weight.

Figure 3:
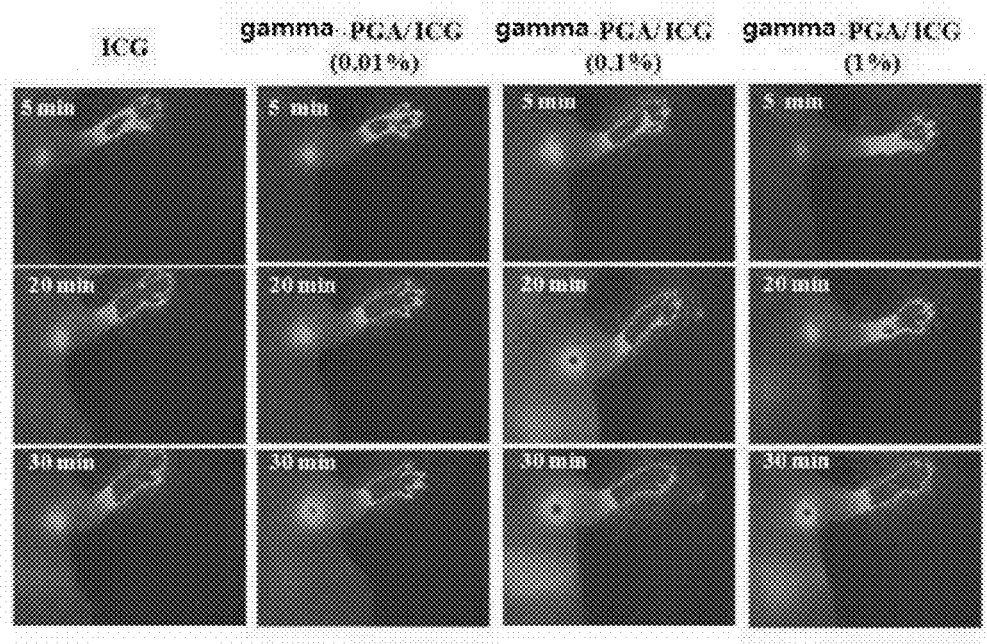
FIG. 3 shows in vivo sentinel lymph node images obtained by a near-infrared optical imaging system at 5-30 minutes after injecting a γ-PGA (MW: 50 kDa)/ICG complex into the left forefeet of mouse.
Figure 4:
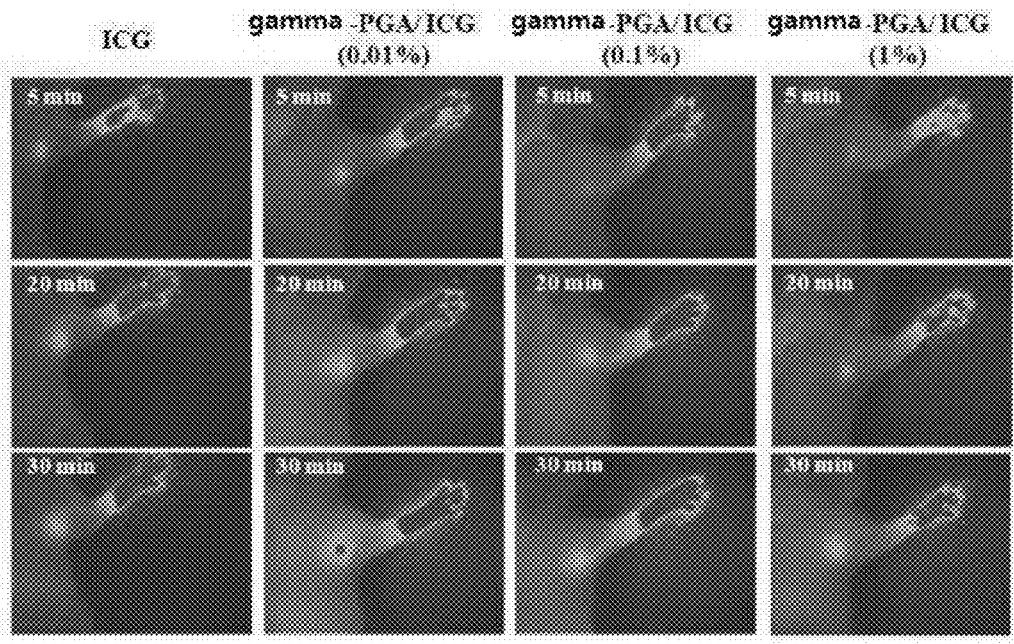
FIG. 4 shows in vivo sentinel lymph node images obtained by a near-infrared optical imaging system at 5-30 minutes after injecting a γ-PGA (MW: 7000 kDa)/ICG complex into the left forefeet of mice.

In an example of the present invention, γ-PGA/ICG complexes having molecular weights of 50 kDa and 7000 kDa, respectively, were prepared and applied for the detection of the sentinel lymph node (see FIGS. 3 and 4).

As shown in FIG. 3, when ICG alone was injected into the skin, it showed a tendency to migrate toward the sentinel lymph node with the passage of time, but even after 30 minutes after the injection, ICG did not remain in the sentinel lymph node and migrated to other lymph node, indicating that the intensity of fluorescence emitted from the sentinel lymph node is very weak. However, when the γ-PGA (MW: 50 kDa)/ICG complex was injected into the skin at a concentration of 0.01%, the intensity of fluorescence emitted from the sentinel lymph node after 30 minutes was very strong.

In addition, when the γ-PGA/ICG complex was injected at an increased concentration of 0.1%, a strong fluorescence signal started to be detected in the sentinel lymph node from 5 minutes after the injection, and a very strong fluorescence signal could be detected after 20 and 30 minutes. However, when the γ-PGA/ICG complex was injected at a concentration of 1%, a weak signal appeared before 20 minutes after the injection, and a strong fluorescence signal could be detected in the sentinel lymph node after 30 minutes after the injection.

FIG. 4 shows the fluorescence intensity detected in the sentinel lymph node after injecting a γ-PGA (MW: 7000 kDa)/ICG complex into the skin at concentrations of 0.01%, 0.1% and 1%.

As can be seen in FIG. 4, when the γ-PGA (MW: 7000 kDa)/ICG complex was injected at a concentration of 0.01%, a strong fluorescence signal started to be detected in the sentinel lymph node from 20 minutes after the injection, and the signal became stronger after 30 minutes. However, when the γ-PGA (MW: 7000 kDa)/ICG complex was injected at concentrations of 0.1% and 1%, the signal detected in the sentinel lymph node was weak.

The above test results suggest that, in the method of detecting the sentinel lymph node using the γ-PGA/ICG complex, it is very important to suitably select the concentration of the complex according to the molecular weight of γ-PGA.

EXAMPLES

Hereinafter, the present invention will be described in further detail with reference to examples. It will be obvious to a person having ordinary skill in the art that these examples are illustrative purposes only and are not to be construed to limit the scope of the present invention.

Example 1

Preparation of PGA/ICG Complex

Indocyanine green which is used as a fluorescent dye is an anionic amphipathic (hydrophobic and hydrophilic) material. The negative charge of indocyanine is hydrophobically (non-covalently) coupled to the hydrophobic moiety of poly-gamma-glutamic acid (γ-PGA) in an aqueous solution to form a complex.

A complex of indocyanine green (ICG) and γ-PGA was prepared in the following manner.

1.01 mg of ICG (Dongindanq Pharmaceutical Co., Ltd.) and each of 0.1, 1 and 10 mg of γ-PGA (Bioleaders Corp.) were dissolved in 1 ml of triple-distilled water to prepare a complex.

50 μl of the prepared ICG/γ-PGA complex solution was dispensed into a 1.5 Ml tube, and then the near-infrared fluorescence spectrum thereof was measured using a fluorescence spectrophotometer (FluoroMate FS-2) (see FIG. 1).

As can be seen in FIG. 1, the fluorescence intensity of ICG alone rapidly decreased with the passage of time, but the fluorescence intensity of the ICG/γ-PGA complex was maintained at a substantially constant level even after 3 days.

Example 2

In Vivo Imaging of ICG/γ-PGA Complex

In animal tests, 6-week-old female BALB/c nude mice (SLC Inc., Japan) with no pathogens were used. All the tests were performed under the approval of the Laboratory Animal Center, Chungnam National University.

Figure 2:
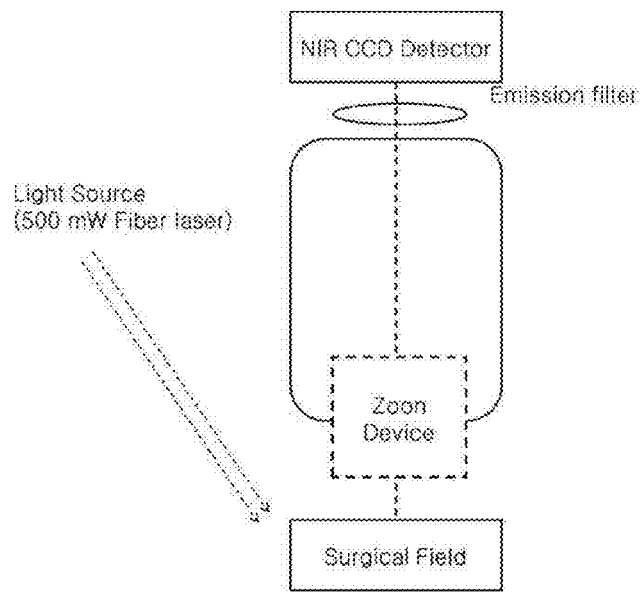
FIG. 2 is a schematic view of a near-infrared imaging device used in the present invention.

For data acquisition and analysis, images (see FIG. 3) were obtained using a home-made NIR optical imaging system (see FIG. 2) manufactured by the present inventors. Herein, the near-infrared optical imaging system comprises a light source consisting of a 500 mW fiber-type laser, an emission filter, a lens system equipped with a microzoom, and a near-infrared detector (NIR CCD detector) (see FIG. 2). In the near infrared imaging system, the intensity of fluorescence appears as a pseudo color, and more red fluorescence indicates stronger intensity.

Before imaging, mice were anesthetized by intraperitoneally injecting a 2.5% avertin (2,2,2-tribromoethanol-tert-amyl alcohol, Sigma) solution at a dose of 0.01 Ml/g weight. 50 μl of each of an ICG solution (0.01%), ICG/γ-PGA (50 kDa) complex solutions (0.01%, 0.1% and 1%) and ICG/γ-PGA (7000 kDa) complex solutions (0.01%, 0.1% and 1%) was injected into the left forefoot of each nude mouse (footpad, subcutaneous injection), and after 5 min, 20 min and 30 min, the fluorescence of the sentinel lymph node was measured. All the near-infrared fluorescence images were measured using a 760 nm laser and an 835/55 nm (excitation wavelength: 810-860 nm) filter set.

As a result, as can be seen in FIG. 3, when ICG alone was injected into the skin, it showed a tendency to migrate toward the sentinel lymph node with the passage of time, and even after 30 minutes after the injection, ICG did not remain in the sentinel lymph node and migrated to other lymph node, indicating that the intensity of fluorescence emitted from the sentinel lymph node is very weak. However, when the γ-PGA (MW: 50 kDa)/ICG complex was injected into the skin, the intensity of fluorescence emitted from the sentinel lymph node after 30 minutes was very strong compared to that in the use of ICG alone.

In addition, when the γ-PGA/ICG complex was injected at an increased concentration of 0.1%, a strong fluorescence signal started to be detected in the sentinel lymph node from 5 minutes after the injection, and a very strong fluorescence signal could be detected after 20 and 30 minutes. However, when the γ-PGA/ICG complex was injected at a concentration of 1%, a weak signal appeared before 20 minutes after the injection, and a strong fluorescence signal could be detected in the sentinel lymph node after 30 minutes after the injection.

FIG. 4 shows the fluorescence intensity detected in the sentinel lymph node after injecting a γ-PGA (MW: 7000 kDa)/ICG complex into the skin at concentrations of 0.01%, 0.1% and 1%. As can be seen in FIG. 4, when the γ-PGA/ICG complex was injected at a concentration of 0.01%, a strong fluorescence signal started to be detected in the sentinel lymph node from 20 minutes after the injection, and the signal became stronger after 30 minutes. However, when the γ-PGA (MW: 7000 kDa)/ICG complex was injected at concentrations of 0.1% and 1%, the signal detected in the sentinel lymph node was weak.

The above test results suggest that, in the method of detecting the sentinel lymph node using the γ-PGA/ICG complex, it is very important to suitably select the concentration of the complex according to the molecular weight of γ-PGA.

INDUSTRIAL APPLICABILITY

As described above, the present invention provides a poly-gamma-glutamic acid/fluorescent dye complex, which contains no radiopharmaceutical and is harmless to the human body. The use of the poly-gamma-glutamic acid/fluorescent dye complex makes it possible to accurately detect the position of a sentinel lymph node in real time without concerns about radioactive contamination.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. An optical imaging probe for detecting a sentinel lymph node, which contains a complex of poly-gamma-glutamic acid and indocyanine green (ICG),
   wherein a negative charge of the indocyanine green (ICG) is hydrophobically coupled to hydrophobic moiety of the poly-gamma-glutamic acid in an aqueous solution,
   the poly-gamma-glutamic acid has a molecular weight of 10-15000 kDa, and
   a concentration of the complex of poly-gamma-glutamic acid and indocyanine green (IGC) depends on a molecular weight of the poly-gamma-glutamic acid.

* * * * *